United States Patent
Koiwai et al.

(10) Patent No.: US 7,297,475 B2
(45) Date of Patent: Nov. 20, 2007

(54) MEDICAMENT INJECTION KIT AND MEDICAMENT INJECTION METHOD

(75) Inventors: Kazunori Koiwai, Kanagawa (JP); Tetsuo Tanaka, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 274 days.

(21) Appl. No.: 10/840,600

(22) Filed: May 7, 2004

(65) Prior Publication Data

US 2004/0253212 A1    Dec. 16, 2004

(30) Foreign Application Priority Data

May 16, 2003    (JP)    ............... 2003-138465

(51) Int. Cl.
| | |
|---|---|
| *A01N 1/00* | (2006.01) |
| *A01N 1/02* | (2006.01) |
| *C12N 15/63* | (2006.01) |
| *A61M 25/10* | (2006.01) |

(52) U.S. Cl. .................. 435/1.2; 604/915; 604/919; 435/455; 514/2; 514/44

(58) Field of Classification Search ............ None
See application file for complete search history.

(56) References Cited

U.S. PATENT DOCUMENTS

| | | | |
|---|---|---|---|
| 4,897,355 A | | 1/1990 | Eppstein et al. |
| 5,334,761 A | | 8/1994 | Gebeyehu et al. |
| 5,741,248 A | * | 4/1998 | Stern et al. ............ 606/21 |
| 5,792,094 A | * | 8/1998 | Stevens et al. ............ 604/4.01 |
| 6,699,231 B1 | * | 3/2004 | Sterman et al. ............ 604/509 |

FOREIGN PATENT DOCUMENTS

| | | |
|---|---|---|
| JP | 07-304796 | 11/1995 |
| JP | 08-023982 | 1/1996 |

OTHER PUBLICATIONS

P. Heikkila et al., "Adenovirus-Mediated Gene Transfer into Kidney Glomeruli Using an Ex Vivo and In Vivo Kidney Perfusion System-First Steps Towards Gene Therapy of Alport Syndrome", Gene Therapy, 1996, pp. 21-27, vol. 3, Stockton Press.
K. O'Hare et al., "Transformation of Mouse Fibroblasts to Methotrexate Resistance By a Recombinant Plasmid Expressing a Prokaryotic Dihydrofolate Reductase", Proc. Natl. Acad. Sci. USA, 1981, pp. 1527-1531, vol. 78, No. 3, USA.
Hitoshi Niwa et al., "Efficient Selection for High-Expression Transfectants With a Novel Eukaryotic Vector", Gene., 1991, pp. 193-200, vol. 108, Elsevier Science Publishers B.V.

* cited by examiner

*Primary Examiner*—Quang Nguyen
(74) *Attorney, Agent, or Firm*—Buchanan Ingersoll & Rooney PC

(57) ABSTRACT

A medicament injection kit, for use in occluding a renal artery and a renal vein in a kidney and injecting a therapeutic medicament into the kidney so as to pressurize the kidney, includes: an artery catheter which includes a first balloon capable of occluding the renal artery; a vein catheter which includes a second balloon capable of occluding the renal vein; a syringe for injecting the therapeutic medicament, the syringe being capable of being connected to at least one of the artery catheter and the vein catheter; and a syringe for pressurizing the inside of the kidney by injecting a liquid, the syringe being capable of being connected to at least one of the artery catheter and the vein catheter.

6 Claims, 1 Drawing Sheet

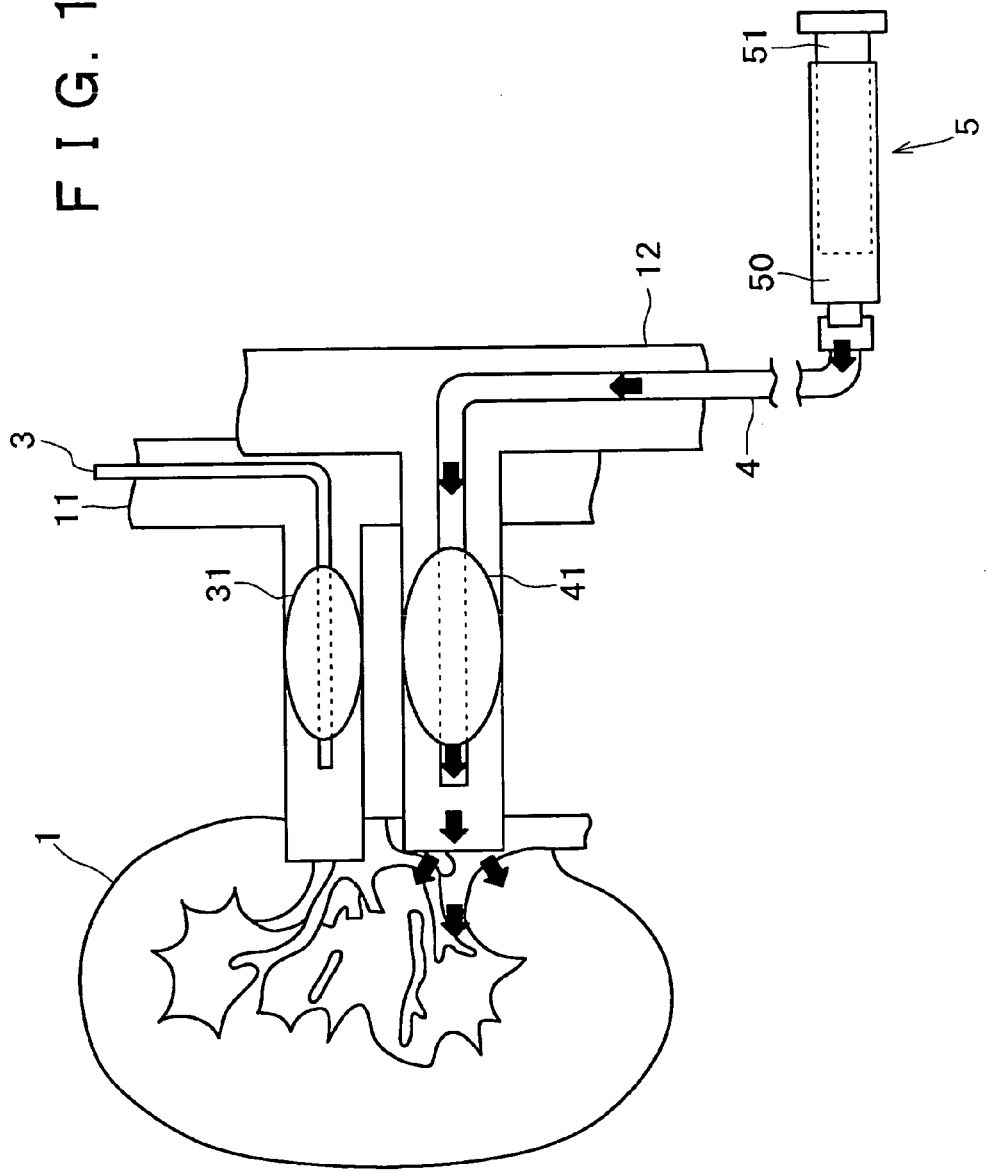

MEDICAMENT INJECTION KIT AND MEDICAMENT INJECTION METHOD

BACKGROUND OF THE INVENTION

The present invention relates to a medicament injection kit for injecting a therapeutic medicament into a tissue in a living body. More specifically, the present invention relates to a medicament injection kit for injecting a therapeutic medicament, which is used for introducing a gene into a tissue in a living body without using viral vectors.

Since around 1990, in the United States, there has been proposed the gene therapy for treating diseases such as cancer by introducing a gene into cells in a living body. In the gene therapy, it is most important to efficiently introduce the intended gene into the target cells. The methods for introducing a gene into cells are generally classified into two types: the type in which viral vectors are used (see, for example, Heikkila P. et al., (England), Gene Therapy, 1996, Vol. 3, pp. 21-27), and the type in which viral vectors are not used (see, for example, U.S. Pat. Nos. 4,897,355 and 5,334,761).

The method using viral vectors has been used most widely until recently, because the method has been considered to be the most effective from the viewpoints of high introduction efficiency. In the efficiency of introduction of a gene into cells, the method using viral vectors is much higher than the other methods in which viral vectors are not used; thus, the method using viral vectors has been the most excellent in efficiency.

A typical one of the methods not using viral vectors is the liposome method, in which a chemically synthesized lipid is used. This method is high in safety, and has been developed to be very high in introduction efficiency ex vivo, particularly. Agents used in the liposome method can be synthesized inexpensively, and it is considered to be excellent introduction means suited to mass preparation.

Besides, only in the case of a muscle, there has also been practiced a method of plasmid direct injection. This method has been reported to be clinically effective for angiogenesis in the heart, particularly.

However, the gene introduction method using viral vectors involves a problem as to safety, and may be attended by a severe side effect; therefore, a new protocol for this method is not approved at present. On the other hand, the gene introduction methods not using a viral vectors are unsatisfactory in introduction efficiency in vivo, give small gene expression amounts in cells and are limited in therapeutic effect, though the method are very high transfection efficiency ex vivo. Particularly, the method using a naked plasmid is low in the efficiency of introduction into cells and is considered to be difficult to put into practical use, though the method is extremely high in safety.

SUMMARY OF THE INVENTION

The present invention has been made in consideration of the above-mentioned problems involved in the prior art. Accordingly, it is an object of the present invention to provide a medicament injection kit, and a medicament injection method, by which a therapeutic medicament can be injected into a target tissue safely and efficiently in vivo. More specifically, it is an object of the present invention to provide a medicament injection kit, and a medicament injection method, by which a gene can be introduced into cells in a target tissue safely and efficiency in vivo, with the result of expression of the gene over a wide range of the cells.

In accordance with one aspect of the present invention, there is provided a medicament injection kit for use in occluding an artery and a vein in a target tissue and injecting a therapeutic medicament into the occluded target tissue so as to pressurize the target tissue, the medicament injection kit including: a catheter for artery which includes first blood vessel occluding means capable of indwelling in a blood vessel; a catheter for vein which includes second blood vessel occluding means capable of indwelling in a blood vessel; means for injecting the therapeutic medicament, the injecting means being capable of being connected to at least one of the catheter for artery and the catheter for vein; and means for pressurizing the inside of a blood vessel by injecting liquid, the pressurizing means being capable of being connected to at least one of the catheter for artery and the catheter for vein.

In the medicament injection kit of the present invention, the first and the second blood vessel occluding means are each preferably a balloon.

In the medicament injection kit of the present invention, the means for injecting the therapeutic medicament and the means for pressurizing the inside of the blood vessel are preferably composed of single means.

In the medicament injection kit of the present invention, the liquid is preferably a therapeutic medicament, physiological saline, Ringer's solution, an infusion or a mixture thereof.

In the medicament injection kit of the present invention, the therapeutic medicament is preferably at least one selected from the group consisting of nucleic acid, polynucleotide, gene, analog thereof, and a complex of a synthetic vector such as liposome and polymer with gene.

In accordance with another aspect of the present invention, there is provided a method of injecting a therapeutic medicament into a target tissue, comprising the following steps (a) to (d): (a) inserting a catheter for vein including vein occluding means into a vein in the target tissue, and occluding the vein in the target tissue by the vein occluding means; (b) injecting the therapeutic medicament into the target tissue from said catheter for vein; (c) inserting a catheter for artery including artery occluding means into an artery in the target tissue, and occluding the artery in the target tissue by the artery occluding means; and (d) pressurizing the target tissue by injecting a liquid into the target tissue from said catheter for vein or said catheter for artery.

In the above method, the vein occluding means and the artery occluding means are each preferably a balloon.

In accordance with a further aspect of the present invention, there is provided a method of injecting a therapeutic medicament into a target tissue, comprising the following steps (a) to (d): (a) inserting a catheter for artery including artery occluding means into an artery in the target tissue, and occluding the artery in the target tissue by the artery occluding means; (b) injecting the therapeutic medicament into the target tissue from said catheter for artery; (c) inserting a catheter for vein including vein occluding means into a vein in the target tissue, and occluding the vein in the target tissue by the vein occluding means; and (d) pressurizing the target tissue by injecting a liquid into the target tissue from said catheter for artery or said catheter for vein.

In the above method, the artery occluding means and the vein occluding means are each preferably a balloon.

According to the present invention, a therapeutic medicament can be injected in vivo into a target tissue safely and efficiently. Particularly, where the therapeutic medicament is a gene-therapeutic medicament used for the purpose of introducing a desired gene into cells in a target tissue without using viral vectors, the gene can be introduced into the cells safely and a high transfection efficiency is observed. Specifically, according to the present invention, a plasmid which is widely known to be low transfection efficiency in vivo can be introduced into the cells at a very high transfection efficiency.

Besides, according to the present invention, in which internally pressurizing a target tissue in the condition where the bloodstream in the target tissue is blocked after a therapeutic medicament has been injected into the target tissue, the procedure can be carried out by use of low-invasiveness means.

The above and other objects, features and advantages of the present invention will become apparent from the following description and appended claims, taken in conjunction with the accompanying drawing which shows by way of example a preferred embodiment of the invention.

BRIEF DESCRIPTION OF THE DRAWING

FIG. 1 is an illustration of the method of using a medicament injection kit according to the present invention, where a kidney is adopted as a target tissue.

DETAILED DESCRIPTION OF THE PREFERRED EMBODIMENTS

Now, the present invention will be described more in detail below, referring to the drawing. The drawing is for the purpose of exemplification only, and the invention is not limited to the form shown in the drawing.

The medicament injection kit according to the present invention includes a catheter for artery which is used for occluding an artery in a target tissue, and a catheter for vein which is used for occluding a vein in the target tissue. The catheter for artery and the catheter for vein are each provided with blood vessel occluding means capable of indwelling in a blood vessel. Here, the blood vessel occluding means is means for internally occluding a blood vessel when set to indwell at a desired site in the blood vessel. Such blood vessel occluding means is preferably a balloon, since it is widely used for the purpose of occluding a blood vessel, does not damage the site at which it indwells, and can be easily removed by deflation after use.

The catheters and the balloons can be selected from wide ranges of known ones; desired ones may be selected according to the sites in the target tissues and the diameters of the blood vessels to be occluded.

The medicament injection kit according to the present invention includes means for injecting a therapeutic medicament (medicament injecting means) which is capable of being connected to at least one of the catheter for artery and the catheter for vein. The medicament injecting means can load the therapeutic medicament, and, when connected to the catheter for artery or the catheter for vein, it can inject the loaded therapeutic medicament into an artery or vein through a lumen of the catheter in a desired amount and at a desired injection rate. Specific examples of the medicament injecting means include a syringe. The medicament injecting means may comprise, and preferably includes, means for controlling the injection amount and the injection rate of the therapeutic medicament. Examples of the control means include a syringe pump. The syringe and the syringe pump can be selected from wide ranges of known ones; desired ones may be appropriately selected according to the amount and the injection rate of the therapeutic medicament.

The medicament injection kit according to the present invention includes means for pressurizing the inside of a blood vessel (pressurizing means) which is capable of being connected to at least one of the catheter for artery and the catheter for vein. The pressurizing means is for pressurizing the inside of a blood vessel by injecting a liquid into the blood vessel, and is similar to the medicament injecting means on a function basis. Preferably, the medicament injecting means and the pressurizing means are composed as a single means. Specifically, it is preferable that the blood in the target tissue is substantially replaced with the therapeutic medicament by the medicament injecting means, thereafter the bloodstream in the target tissue is blocked, and, in this condition, the therapeutic medicament is further injected, to thereby internally pressurize the target tissue. This ensures that the kit is simple in configuration, and only a small number of steps are required in operation.

Next, one example of the method of using the medicament injection kit according to the present invention will be described. FIG. 1 is a conceptual drawing for illustrating the method of using the medicament injection kit of the present invention, where a kidney (left kidney) is adopted as a target tissue.

In FIG. 1, first, one of the artery and the vein in the target tissue is occluded by using the catheter and causing the blood vessel occluding means to indwell at a desired position in the artery or vein. For this purpose, in FIG. 1, an artery balloon catheter 3 is inserted into a renal artery 11 of the kidney 1, and a vein balloon catheter 4 is inserted into a renal vein 12.

Subsequently, one of a balloon 31 of the artery balloon catheter 3 and a balloon 41 of the vein balloon catheter 4 is inflated by an ordinary method, to occlude the renal artery 11 or the renal vein 12. In FIG. 1, the balloon 41 of the vein balloon catheter 4 is inflated to occlude the renal vein 12. The one of the vein and the artery which is to be occluded first is selected according to the side on which the therapeutic medicament is to be injected. In the example shown in FIG. 1, the therapeutic medicament is to be injected into the renal vein 12, and, therefore, the renal vein 12 is occluded first. On the other hand, in the case where the target tissue is a muscle, a research of a therapeutic medicament injection without blocking the bloodstream, has reported that it is preferable to inject the medicament from the artery side. In such a case, it is considered to the preferable to occlude the artery first.

In the embodiment shown in FIG. 1, means for injecting the therapeutic medicament (hereinafter referred to the "medicament injecting means") 5 is connected to the vein balloon catheter 4. In FIG. 1, the medicament injecting means 5 is a syringe. After the renal vein 12 is occluded by the balloon 41, a plunger 51 of the medicament injecting means 5 is operated, whereby a therapeutic medicament in an outer tube 50 is injected through a lumen of the vein balloon catheter 4 into the renal vein 12. Since the renal vein 12 is occluded by the balloon 41, the therapeutic medicament is fed through the renal vein 12 into the kidney 1, and then into the renal artery 11. In this manner, the blood in the target tissue, or in the kidney 1, is substantially replaced with the therapeutic medicament.

After the blood in the kidney 1 is replaced with the therapeutic medicament, the balloon 31 of the artery balloon catheter 3 is inflated to occlude the renal artery, whereby the bloodstream in the target tissue (the kidney 1) is blocked. At this point, the inside of the target tissue (the kidney 1) has been substantially filled with the therapeutic medicament. In the method according to the present invention, from this condition, a suitable amount of the therapeutic medicament is further injected, to thereby internally pressurize the target tissue (the kidney 1).

Here, the amount of the therapeutic medicament injected for the purpose of pressurizing the target tissue is a volume for sufficiently pressurizing the target tissue, and, based on the volume of the target tissue, the amount is preferably 10 to 150% based on the volume, more preferably 20 to 100% based on the volume, and further preferably 40 to 80% based on the volume.

It should be noted that the above-mentioned pressurizing is achieved when the target tissue is filled with the therapeutic medicament and then pressurized internally and sufficiently. For example, there may be adopted a method in which, after the blood in the target tissue is replaced with the therapeutic medicament and the bloodstream in the target tissue is blocked, a liquid compatible with the living body, for example, physiological saline or the like is injected into the target tissue by use of the medicament injecting means 5 or other similar means, to thereby internally pressurize the target tissue.

Here, the operation of injecting the therapeutic medicament for replacing the blood in the target tissue with the therapeutic medicament and the subsequent operation of injecting the therapeutic medicament or other liquid for the purpose of pressuring the target tissue may be utterly independent operations. For example, in the embodiment shown in FIG. 1, there may be adopted a method in which, after the therapeutic medicament is injected from the medicament injecting means 5 connected to the vein balloon catheter 4 to thereby replace the blood in the target tissue with the therapeutic medicament and the balloon 31 of the artery balloon catheter 3 is inflated to block the bloodstream in the target tissue, means similar to the medicament injecting means 5 is connected to the artery balloon catheter 3, and a liquid compatible with the living body is injected into the renal artery 11 by use of the means to thereby pressurize the target tissue.

After the condition where the target tissue is thus pressurized is maintained for a desired period of time, the balloons 31 and 41 are deflated, to thereby restart the bloodstream in the target tissue. The period of time under the condition of pressurization of the target tissue is in such a range that the effect of the therapeutic medicament is sufficient and that the tissue is not damaged due to the blocking of the bloodstream. The period of time differs depending on the kind of the target tissue and the range of the target tissue (in the case where the target tissue is an organ such as kidney, whether the therapeutic medicament is to be injected into the whole part of the organ or to be injected into a part of the organ). The period of time is normally up to 2 min, preferably up to 1 min, and more preferably up to 30 sec.

Accordingly, it is preferable to carry out the pressurization of the target tissue in a short time. Specifically, the above-mentioned injection of the therapeutic medicament into the target tissue is preferably carried out in 1 min, more preferably in 30 sec. Where the pressurization is carried out in a short time, the effect of pressurizing the target tissue is better as compared with the case of injecting the liquid over a long period of time, even if the amount of the liquid injected is the same.

The therapeutic medicament injected into a target tissue by the medicament injection kit according to the present invention includes a wide variety of medicaments injected for therapeutic or prophylactic purposes, and is selected according to a patient. Specific examples of the medicament include antibiotics, vitamin agents (comprehensive vitamin agent), amino acids, anti-thrombus agents such as heparin, insulin, antitumor agents, analogetic, cardiac, phloboclysis anesthetic, anti-parkinsonism agent, ulcer curing agents, adrenocortical hormone agents, arrhythmia curing agents, correcting electrolytes, virucides, immunoenhancers, gene-therapeutic agents, etc.

Among the above examples, preferred are gene-therapeutic medicaments, specifically those gene-therapeutic medicaments which are used for introducing a gene into a target tissue without use of viral vectors.

Specific examples of such a gene-therapeutic medicaments include nucleic acid, polynucleotide, genes including plasmids, analog thereof, complexes of a synthetic vector such as liposome and polymer with a gene, etc.

The method of introducing a gene into cells by use of such a gene-therapeutic medicament without using viral vectors is safe because it does not use viral vectors, but is low in introduction efficiency in vivo.

When the medicament injection kit according to the present invention is used, by replacing the blood in a target tissue with a therapeutic medicament, then blocking the bloodstream in the target tissue and internally pressurizing the target tissue under this condition, it is possible to improve the transfection efficiency in introducing a gene into cells in the target tissue by use of the above-mentioned gene-therapeutic medicament.

Among the above-mentioned gene-therapeutic medicaments, preferred are plasmids coding a desired gene in a mammal expression vector. With a desired structural gene coded in a plasmid, expression of a desired protein in the cells in the target tissue can be achieved without using a vector such as virus and liposome. Preferred examples of the expression vector include pSVL expression vector (Pharmacia Y.K), pSG expression vector (JP 7-304796 A and JP 8-23982 A), pKCR expression vector (K. O'Hare, et al., Proc. Natl. Acad. Sci. USA, 78, 1527, 1981), pCAGGS expression vector (H. Niwa, et al., Gene, 108, 193, 1991), etc.

Examples of the structural gene to be used include gene of vascular endothelial cell growth factor (VEGF) which has angiogenesis activity and is considered to be effective for treatment of arteriosclerosis, gene of hepatocyte growth factor (HGF), gene of fibroblast growth factor (FGF), etc. Arteriosclerosis causes stenosis of peripheral vessels and, when gravy, needs B-K amputation. Such a patient can be treated by a method, through muscular injection, with a mammal cell expression plasmid coding the angiogenesis activity as above-mentioned, that produces the proteins having the angiogenesis activity in the muscular cells, thereby promoting the collateral vessel growth (bypasses). Similarly, myocardial infarction can be treated by injecting into cardiac muscles with a mammal cell expression vector coding a gene of angiogenesis activity factor so as thereby to promote the collateral vessel growth (bypasses).

Other structural genes can also be used, examples of which include gene of dystrophin which is mutated in muscular dystrophy, gene of erythropoietin which is a cytokine acting on erythroid cells and is useful for treating anemia of chronic renal faluer, gene of blood coagulation factor VIII/IX which is effective for treatment of hemophiliac, gene of insulin which is effective for treatment of insulin-dependent diabetic, and gene of decolin for inhibiting the transforming growth factor-β (TGF-β) which is considered to promote fiberization in a variety of fibrosis. Besides, reporter genes such as β-galactosidase, luciferases, chloramphenicol acetyl transferase, etc. can also be used. Further, when genes of constitutive proteins of infectious phathogenic microorganisms such as viruses and bacteria are used as the structural genes, they can be used as DNA vaccines. Antisenses can also be used; for example, Duchenne type muscular dystrophy due to deletion of exon can be treated by use of antisense with a splicing acceleration alignment.

Incidentally, the target tissue, into which a therapeutic medicament is to be injected by use of the medicament injection kit according to the present invention is not limited to the kidney shown in the drawing, and can be selected from a wide variety of tissues in the living body. Examples of the target tissue include not only organs such as kidney, heart, lever, brain, etc. but also muscular tissues.

Here, the artery and vein to be occluded can be appropriately selected according to the kind of the target tissue and the range of the target tissue (where the target tissue is an organ such as kidney, whether the therapeutic medicament is to be injected into the whole part of the organ or to be injected into a part of the organ).

For instance, where the target tissue is an organ such as the kidney (left kidney) 1 as in the embodiment shown in FIG. 1 and where the therapeutic medicament is to be injected into the whole part of the organ, the artery (renal artery) 11 and the vein (renal vein) 12 which feed all the area of the organ are occluded. In the case of injecting the therapeutic medicament only into a specified site in an organ, an artery and a vein to be occluded are selected in relation to the specified site.

Depending on the organ, there may be a plurality of sets of artery and vein which constitute the interstitial area. For example, in the case of the heart, there are two arteries (right coronary artery and left coronary artery). Therefore, in case the target tissue is a heart and the therapeutic medicament is to be injected into the whole part of the heart, both the right coronary artery and the left coronary artery are occluded. On the other hand, in case the therapeutic medicament is to be injected into a feeding area of only one of the two coronary arteries, only the coronary artery is occluded.

When the medicament injection kit according to the present invention is used, the blood in the target tissue is substantially replaced with the therapeutic medicament, then the bloodstream in the target tissue is blocked, and, under this condition, the target tissue is internally pressurized; therefore, it is possible to effectively inject the therapeutic medicament into the target tissue. Particularly, where the therapeutic medicament is a gene-therapeutic medicament used for the purpose of introducing a desired gene into cells in a target tissue without use of viral vectors, the gene can be introduced into the cells safely and at a high transfection efficiency. More particularly, by use of the medicament injection kit of the present invention, plasmids which are widely known to be low in the efficiency of introduction into cells in vivo can be introduced into the cells at a very high transfection efficiency.

In the case of using the medicament injection kit according to the present invention, the bloodstream in the target tissue is blocked not by invasive means such as surgery but by use of the catheters which are via-lumen means; therefore, the blocking of the bloodstream can be achieved with low invasiveness.

EXAMPLES

Now, the present invention will be further described referring to Examples, which are not limitative of the invention.

Example 1

Plasmid

Plasmid pCAGGS-Luc was used as a gene. This plasmid is coding luciferase, which is a reporter gene, incorporated on the downstream side of an enhancer of cytomegalovirus and chicken β-actin/rabbit β-globin. In injection, the plasmid was used in the form of a gene preparation produced by dissolving 10 mg of the plasmid in 30 ml of Ringer's solution (physiological saline).

Animals

Beagles (weight: 10 kg) were purchased from Nihon Ikagaku Doubutsu Shizai Kenkyuujo Inc.

Injection Method

Under X-ray observation, a balloon catheter (artery catheter) was inserted into the renal artery via the crural artery, and the balloon was set to indwell in the renal artery. Similarly, a balloon catheter (vein catheter) was inserted into the renal vein via the crural vein, and the balloon was set to indwell in the renal vein.

After the balloon of the vein catheter was inflated to occlude the renal vein, 10 ml of the gene preparation was injected through the lumen of the vein catheter, to substantially replace the blood in the kidney with the gene preparation.

Immediately thereafter, the balloon of the artery catheter was inflated to occlude the renal artery, thereby blocking the bloodstream into the kidney, and an additional 20 ml of the gene preparation was injected through the lumen of the vein catheter, to pressurize the inside of the blood vessels in the kidney. The volume of the kidney as the target tissue in this example was about 40 ml, and, therefore, the gene preparation in an amount of 50% based on the volume of the kidney was injected for the purpose of pressurization.

This condition was maintained for 30 sec, then the balloons of the artery catheter and the vein catheter were deflated, to restart the bloodstream in the kidney, and the artery catheter and the vein catheter were pulled out of the kidney.

Expression Protein Detection Method

After 48 hr from the injection, the beagle was anatomized, and the kidney was taken out. After the kidney was minced to an appropriate size, the minced piece was immersed in a Picagene cell extract (a product by Toyo Ink MFG. CO., LTD.), and a tissue extract was prepared by use of Polytron. The luciferase content in the tissue extract was measured by Picagene Luciferase Assay System (a product by Toyo Ink MFG. CO., LTD.). The result was given in Table 1.

In addition, measurement of the amount of luciferase was conducted in the same manner as above, for the case where the gene preparation was injected by occluding neither the renal artery nor the renal vein (Comparative Example 1) and for the case where the gene preparation was injected by occluding only the renal vein with the balloon (Comparative Example 2). The results are given in Table 1.

TABLE 1

|  | Amount of luciferases (count/mg protein) |
| --- | --- |
| Comparative Example 1 | 0 |
| Comparative Example 2 | 34020 |
| Example 1 | 120861 |

Results

As shown in Table 1, in Comparative Example 1 where the gene preparation was injected through the renal vein without blocking the bloodstream, expression of luciferase in the kidney was not observed at all. Besides, in Comparative Example 2 where the gene preparation was injected by occluding only the renal vein, expression of luciferase in the kidney was observed, but the expression amount was very small. On the contrary, in Example 1 where both the renal artery and the renal vein were occluded after the injection of the gene preparation and then the inside of the blood vessels in the kidney was pressurized, the expression amount of luciferase in the kidney was increased remarkably.

Example 2

Injection of a gene preparation was conducted in the same manner as in Example 1, except that the gene was changed to plasmid pCAGGS-EPO for coding erythropoietin, and the concentration of erythropoietin in the blood was measured by the EIA method. In addition, measurement of the concentration of erythropoietin in the blood was conducted in the same manner as above, for the case where the gene preparation was injected by occluding neither the renal artery nor the renal vein (Comparative Example 3) and for the case where the gene preparation was not injected at all (Comparative Example 4). The results are given in Table 2.

TABLE 2

| | Concentration of erythropoietin in blood (IU/ml) |
|---|---|
| Comparative Example 3 | 21.4 ± 1.2 |
| Comparative Example 4 | 22.0 ± 1.5 |
| Example 2 | 67.6 ± 13.0 |

Results

As shown in Table 2, the concentration of erythropoietin in the blood in Comparative Example 3 where the gene preparation was injected through the renal vein without blocking the bloodstream is comparable to that in Comparative Example 4 where the gene preparation was not injected at all. From this it is clearly seen that little expression of the gene was achieved in Comparative Example 3. In contrast to this, in Example 2 where both the renal artery and the renal vein were occluded after the injection of the gene preparation and then the additional amount of the gene preparation was injected to pressurize the inside of the blood vessels in the kidney, the concentration of erythropoietin in the blood was increased remarkably.

The present invention is not limited to the details of the above described preferred embodiments. The scope of the invention is defined by the appended claims and all changes and modifications as fall within he equivalence of the scope of the claims are therefore to be embraced by the invention.

What is claimed is:

1. A method of injecting a therapeutic medicament into a kidney, comprising:
   (a) inserting a vein catheter including a first balloon into a renal vein, and occluding said renal vein by said first balloon;
   (b) injecting said therapeutic medicament into said kidney from said vein catheter after (a);
   (c) inserting an artery catheter including a second balloon into a renal artery, and occluding said renal artery by said second balloon after (b); and
   (d) pressurizing said kidney by injecting a liquid into said kidney from said vein catheter or said artery catheter after (c).

2. A method as set forth in claim 1, wherein said liquid is a therapeutic medicament, physiological saline, Ringer's solution, an infusion, or a mixture thereof.

3. A method as set forth in claim 1, wherein said therapeutic medicament is at least one selected from the group consisting of a polynucleotide, a gene, and a complex of a synthetic vector with a gene.

4. A method of injecting a therapeutic medicament into a kidney, comprising:
   (a) inserting an artery catheter including a first balloon into a renal artery, and occluding said renal artery by said first balloon;
   (b) injecting said therapeutic medicament into said kidney from said artery catheter after (a);
   (c) inserting a vein catheter including a second balloon into a renal vein, and occluding said renal vein by said second balloon after (b); and
   (d) pressurizing said kidney by injecting a liquid into said kidney from said artery catheter or said vein catheter after (c).

5. A method as set forth in claim 4, wherein said liquid is a therapeutic medicament, physiological saline, Ringer's solution, an infusion, or a mixture thereof.

6. A method as set forth in claim 4, wherein said therapeutic medicament is at least one selected from the group consisting of a polynucleotide, a gene, and a complex of a synthetic vector with a gene.

* * * * *